United States Patent [19]

Rocher et al.

[11] 4,329,568
[45] May 11, 1982

[54] APPARATUS FOR HEAT TREATMENT, PARTICULARLY THE ASEPTICIZATION, OF CONTACT LENSES

[76] Inventors: Pierre M. Rocher, 36, rue de Picpus, 75012 Paris; Jacques B. Robin, 5, Allée de Flandre, 03200 Vichy, both of France

[21] Appl. No.: 91,830

[22] Filed: Nov. 6, 1979

[30] Foreign Application Priority Data

Nov. 9, 1978 [FR] France ................................ 78 3149

[51] Int. Cl.³ ............................................. H05B 1/02
[52] U.S. Cl. ........................................ 219/497; 236/94; 219/486; 219/505
[58] Field of Search ............... 219/492, 493, 497, 504, 219/505, 508, 521, 441, 483–486; 236/94; 307/117, 113, 115

[56] References Cited

U.S. PATENT DOCUMENTS

| | | | |
|---|---|---|---|
| 1,161,146 | 11/1915 | Mann | 219/508 |
| 1,919,068 | 7/1933 | Lauster | 219/504 |
| 2,180,643 | 11/1939 | Mullin | 219/508 X |
| 3,400,252 | 9/1968 | Hayakawa et al. | 219/505 X |
| 3,898,423 | 8/1975 | Taylor et al. | 219/492 |
| 3,956,978 | 5/1976 | Borley | 219/492 |
| 4,042,805 | 8/1977 | Kopacz et al. | 219/492 |
| 4,135,122 | 1/1979 | Holmquist et al. | 219/492 |
| 4,151,401 | 4/1979 | Van Bokestal et al. | 219/505 |
| 4,165,359 | 8/1979 | Thomas et al. | 219/521 |

*Primary Examiner*—B. A. Reynolds
*Assistant Examiner*—M. H. Paschall
*Attorney, Agent, or Firm*—Charles E. Baxley

[57] ABSTRACT

An apparatus for heat treatment (particularly asepticization) of contact lenses. The apparatus comprises a box having a housing adapted to receive a case for contact lenses and includes an electrical circuit comprising a power supply and at least one heating unit, with the heating unit having a heating resistor and a heat-sensitive switching device. The apparatus is characterized in that it comprises an electronic voltage threshold detection and programmed control.

5 Claims, 2 Drawing Figures

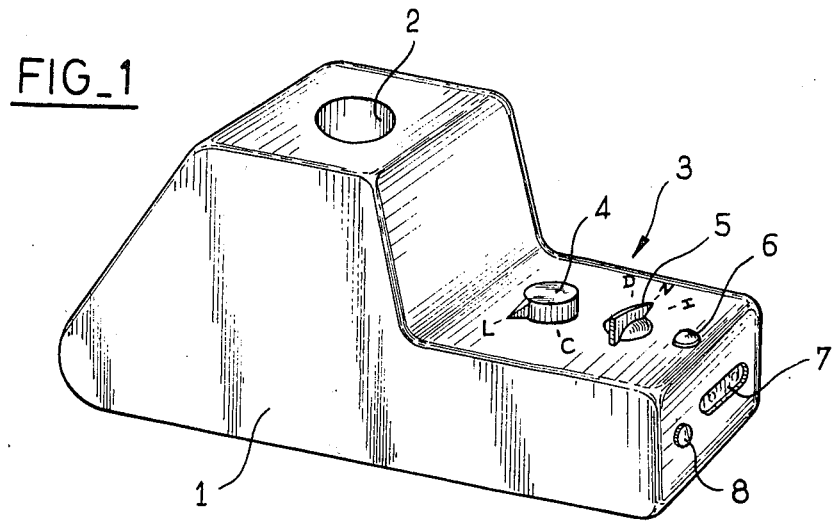
FIG_1
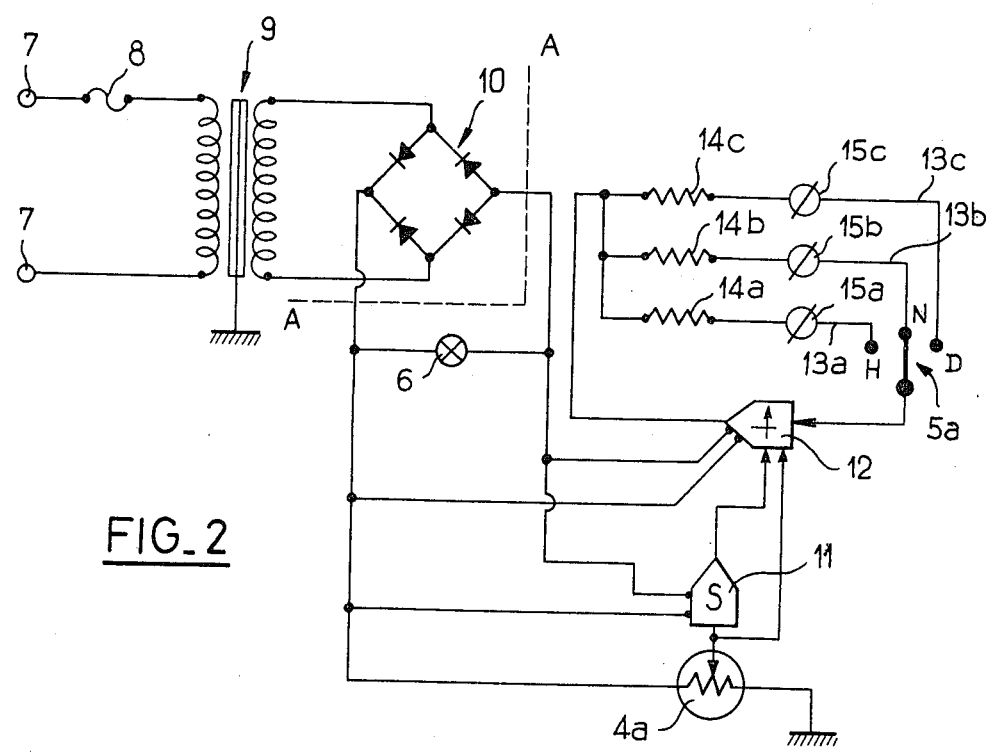
FIG_2

APPARATUS FOR HEAT TREATMENT, PARTICULARLY THE ASEPTICIZATION, OF CONTACT LENSES

The present invention relates to an apparatus for heat treatment, particularly the asepticization, of contact lenses.

Asepticizers known at present have in general the form of a box which:
has a housing adapted to receive a case for contact lenses, and
comprises an electric circuit having:
a power supply and
at least one heating unit.

In another type of asepticizer, the heating unit is formed by a bath of conducting water, through which flows the electric current. Under the effect of the current passing therethrough, the bath of water is brought to, then maintained at, boiling point. The case fitted out with lenses which is immersed in this bath of water or in the steam which is released therefrom is then brought to a temperature close to 100° C.

With the water bath forming one of the elements of the electric circuit, the current flow is interrupted—and the operation terminated—when all the water has evaporated.

The heat cycle of this type of asepticizer is then determined, as far as the level is concerned, by the boiling point temperature of the water and, as far as the duration is concerned, by the time required for total evaporation of the water bath.

In a second type of asepticizer, the heating unit comprises
a heating resistance and
a heat-sensitive switch device.

The switching on of the heating resistance causes heating which, in general, is transmitted through a body having high heat absorption capacity, to a water bath contained in the housing, the case being immersed in this water bath or in the vapour which is released therefrom.

The heat supplied by the heating resistance is absorbed by the water as long as this latter, brought to then maintained at boiling point, has not totally evaporated. Once the evaporation is finished, the heat is no longer absorbed, which causes a temperature detected by the heat-sensitive device. This latter then interrupts the current flow.

As in the preceding case, the heat cycle is determined, as far as the level is concerned, by the boiling point temperature of the water and, as far as the duration is concerned, by the time required for total evaporation of the water bath, even if the interruption of the current flow is not, this time, a direct consequence of this evaporation, but of the choice of temperature threshold for which the heat-sensitive device opens the circuit.

It will be understood that, by means of these two types of apparatus, the lenses may be subjected to a substantially constant temperature, but necessarily close to 100° C., for a duration depending on the amount of water used, as well, in the first case, on the conductivity of this water and on the voltage at the terminals of the apparatus and, in the second case, on the heating power of the resistance and on the quality of the heat transfer.

In a third type of asepticizer, the heat provided by the heating resistance is not absorbed by a water bath, but by a metal element which heats up as long as the resistance is switched on, up to a temperature threshold detected by a heat-sensitive switch device, then yields up the heat thus stored, once the current flow is interrupted.

The heat cycle of this other asepticizer is determined, as far as the level is concerned, by the temperature threshold at which the heat-sensitive switch device interrupts the current flow and, as far as the duration is concerned, by the thermal inertia of the metal element.

Though this type of asepticizer has the advantage, in relation to the preceding ones, of offering greater flexibility insofar as its "useful" operating temperature is concerned, it presents a disadvantage in that it does not allow the lenses to be subjected to a strictly constant temperature for a given time.

There exist then, at the present time, no apparatus capable of maintaining lenses
at a substantially constant temperature of any value
for a precise duration and also of any value.

Now, for the reasons set forth hereafter, it would be very desirable to be able to have at one's disposition such an apparatus.

Thus, it has been discovered that it is neither indispensible nor desirable to subject contact lenses, for example made from hydrogel, frequently to temperatures close to 100° C. for, at such temperatures:
on the one hand, the material may be impaired, and
on the other hand, the proteins of tears, possibly deposited on the lenses, coagulate under the effect of the heat forming a veil which affects adversely not only the optical quality of the lenses but also the comfort of the user.

In an article appearing in the "British Journal of Ophthalmology", Vol. 56, No. 2 pp. 114–119, Dalloz and Hugues recommended, so as not to impair the material of the lenses "raising the temperature of the (asepticization) device to 60° C. over 2 to 3 hours, which is higher than the required temperature, and that the temperature remain for 30 minutes at this level, which also represents a longer duration than what is really required" to obtain the destruction of germs normally found on the lenses.

Drawing inspiration from this data, the applicants have carried out researches to find out if it is not possible to operate at an even lower temperature, below the coagulation threshold of the proteins of tears, so as to avoid formation of the above-mentioned veil, while ensuring a suitable asepticization.

Experimentation has in effect shown them that such an asepticization was possible and an ideal heat cycle has been determined.

Tests related to:
—eleven bacteria:
*Escherichia coli*
*Staphilococcus epidermis*
*Streptococcus faecalis*
*Proteus vulgaris*
*Klebsiella pneumoniae*
*Pseudomonas aeruginosa*
*Bacillus pumilus*
*Bacillus subtilis*
*Bacillus mesentericus*
Salmonellae
Bordetella
—and a fungus:
*Candida albicans*

The results obtained may be resumed in the following way:

the micro-organisms existing in the normal flora of the eye are killed after a cycle of 4 hours at 54° C.,

*Pseudomonas aeruginosa* is killed after a cycle of 4 hours at 56° C., the intestinal bacteria are killed after a cycle which differs according to the bacteria considered and which goes from 56° C. for *Escherichia coli* to 75° C. for the Salmonellae.

It thus appeared then that a "normally" contaminated lens may be asepticized by exposure to a temperature of the order of 54°–56° C. for a period of about 4 hours, whereas an "abnormally" contaminated lens (which may happen when the wearer has an infection: common cold, influenza, intestinal troubles, etc. . . . ) must be subjected to a higher temperature, of the order of 75° C., for the same period of time.

As far as the asepticization is concerned, it would then be desirable to have available an apparatus capable of working under two different sets of operating conditions.

Furthermore, as is known, it is not sufficient to clean and asepticize daily contact lenses made from hydrogel in order to keep them in perfect condition: about once a week, the deposits which settle thereon must be removed (crystalline structures on which are grafted the proteins, mucus and the lipids contained in the tears) and against which daily cleaning products are powerless. This weekly cleaning is accomplished with the help of enzymatic compositions. Since the enzymes serve as catalysers in reactions which result in the removal of the deposits and since, for any reaction, there exists an optimal operating temperature, the applications have carried out researches to see if it was possible to shorten the relatively long weekly maintenance operation by accomplishing it, not at room temperature as is usual, but precisely at the optimal efficiency temperature for the type of enzymatic composition usually used.

It was therefore necessary, in a first stage, to determine this optimal temperature experimentally—which proved to be of the order of 37° C.—and to check whether, in practice, the fact of operating at about 37° C. effectively shortened the period of treatment. It was thus discovered that this period could be brought from 4 hours to 1 hour.

This confirmed then the need of having an apparatus capable of maintaining the lenses at any given temperature for any given period of time, which would not only enable the lenses to be asepticized in satisfactory conditions (respect of the material, absence of veil formation), but also the period of time to be considerably shortened for the weekly maintenance cycle.

To these technical demands were added other requirements:

the apparatus must be compact, being used daily and possibly carried when travelling; and, the apparatus must be reasonably priced.

It is the provision of such an apparatus that the invention has fixed as its aim.

This aim is reached in that the apparatus of the invention is characterized in that it comprises an electronic voltage threshold detection and programmed control device.

In a preferred embodiment, the apparatus is fed with DC or rectified current and the electronic voltage threshold and programmed control device is formed by a unit comprising an integrator connected firstly, to the power supply secondly, to a potentiometer, and thirdly, to a threshold detector inserted in the heating unit's circuit, said integrator delivering an output voltage which is compared to the switching value of the threshold detector, which value is fixed by the potentiometer, the threshold detector switching while interrupting the current flow when said output voltage equals said value.

This type of device offers, among other advantages, that of providing resetting by simple disconnection of the apparatus.

The electric current supply may be provided from the mains, through a transformer and rectifying bridge, the heating unit thus being supplied, for example, with 5 to 10 Volts. This low voltage, which allows commercial batteries to be substituted for connection to the mains, is made possible by the use of heating resistors developing a low power (of the order of $\frac{1}{4}$ W to $\frac{1}{2}$ W).

As was seen above, it is desirable to be able to operate the apparatus in different modes.

The electric circuit will comprise then advantageously several heating units, the apparatus being provided with a switch for selecting, depending on the desired mode of operation, that one or those ones of the units to be switched on.

Thus, a first heating unit may be controlled so as to maintain a temperature between 30° and 40° C. and switched on when it is required to accomplish the weekly enzymatic treatment or "anti-deposit" treatment of the lenses.

A second heating unit may be controlled so as to maintain a temperature between 56° and 58° C. and switched on when it is required to asepticize lenses contaminated by the normal bacterial flora of the eye.

Finally, a third heating unit may be controlled so as to maintain a temperature between 85° and 100° C. when it is required to asepticize lenses belonging to a wearer whose state of health may cause an abnormal contamination to be suspected. In this case, and to avoid coagulation of the proteins possibly deposited on the lenses, the asepticization cycle will be advantageously preceded by an anti-deposit treatment cycle. Recourse will also be had to asepticization at 85° to 100° C. when the lenses have not been worn for a long time.

Advantageously, the heat-sensitive device with which the apparatus is provided is formed by a thermistor of the PCT type chosen according to the temperature to be maintained constant. As is known, thermistors of this type have the peculiarity of offering a very low resistance as long as they are not exposed to a temperature whose level depends on the special nature of the thermistor considered, and a resistance so high, as soon as this level is reached, and it is opposed to current flow. As soon as the temperature drops below this level, the resistance of the thermistor drops and current flow is re-established.

One embodiment of the invention is described in detail hereafter, with reference to the accompanying drawing in which:

FIG. 1 shows, in perspective, the apparatus of the invention, and

FIG. 2 is an electric circuit diagram included in this apparatus.

If we refer to these figures, it can be seen that the apparatus is formed from a box 1 having a housing 2 adapted to receive a lens case, not shown, and a control panel designated as a whole by reference 3.

This control panel 3 comprises an adjusting knob 4 having two end positions C and L which correspond respectively to a short cycle (1 hour) and a long cycle (4 hours 30 minutes) for selecting the length of operation of the apparatus, and a switch 5 having three positions D, N and H which correspond respectively to the antideposit treatment (37° to 38° C.), to normal asepticization (56° to 58° C.) and to asepticization at a higher temperature (85° C.), for the selection of the operating temperature of the apparatus.

A visual indicator 6 shows if the apparatus is switched on or not.

The apparatus is provided with terminals 7 for connection to an electric power source, and a fuse 8. The current received by terminals 7 is transformed, by transformer 9, then rectified by a diode rectifier bridge 10.

This rectified current supplies:
a potentiometer 4a controlled by the adjusting knob 4,
an integrator 11 connected to potentiometer 4a and to
 a threshold detector 12 such as for example a transistor, a diode, an operational amplifier, etc . . .
a circuit which comprises
three heating units 13a, 13b and 13c
a selector 5a controlled by switch 5, and
the threshold detector 12.

Each heating unit comprises a heating resistor respectively 14a, 14b and 14c and a thermistor of the PCT type, respectively 15a, 15b and 15c.

Resistors 14a and 14b develop, for example, a power of ½ W and resistor 14c a power of ¼ W.

Thermistors 15a, 15b and 15c have a tripping temperature which, still by way of example, is respectively 85° C., 57°-58° C. and 37°-38° C.

The operation of the apparatus is the following.

For purposes of illustration, reference will be made to an operation for asepticizing normally contaminated lenses.

As a first stage, the apparatus is programmed by putting adjusting knob 4 to position L, which is the same as adjusting the potentiometer 4a so that the integrator 11 trips the threshold detector 12 after 4 hours 30 minutes of operation, and by placing switch 5 to position N, which is the same as putting into the circuit heating unit 13b.

After having inserted the case provided with lenses in housing 2, a suitable supply cord connects terminals 7 to the mains, thus supplying the apparatus with AC current at 127 or 220 V. The indicator light 6 lights up, indicating that the apparatus is switched on.

Downstream of transformer 9, the current has a voltage of 10-15 volts and, downstream of the rectifier bridge 10, the supply is provided by rectified DC current having a voltage of 5 to 10 volts.

Whereas the current flow in the heating unit 13b causes a temperature rise, integrator 11 delivers an output voltage which is compared to the tripping value for threshold detector 12, a value which is fixed by potentiometer 4a. When the temperature reaches 57°-58° C., the resistance of thermistor 15b increases sharply and the current flow is interrupted. As soon as the temperature drops below the critical value of 57°-58° C., the resistance of thermistor 15b drops sharply and the current flow is re-established.

When the output voltage of integrator 11 is equal to the tripping value of threshold detector 12, this latter interrupts the current flow.

The asepticization operation is then finished: it has lasted exactly 4 hours 30 minutes, 1 hour 30 minutes for raising the temperature and 3 hours for maintaining at the temperature of 57°-58° C.

It is to be noted that the period of time for raising the temperature may be shortened or lengthened by acting on the nature and the volume of the body which transmits the heat to the case.

The operating principle is strictly the same for higher temperature asepticization (adjusting knob 4 on position L and switch 5 on position H) or for the anti-deposit treatment (adjusting knob 4 on position C and switch 5 on position D).

It is to be noted that the circuit which has just been described is given solely by way of example, to facilitate understanding of the invention and that modifications may be made thereto.

A possible variation consists in supplying with current the heating circuit and the timing unit by means of commercial batteries, instead of using mains current, transformed and rectified.

The same apparatus may, furthermore, be designed so that it may be supplied with current selectively in one or the other way.

The possibility of battery operation is obviously advantageous for an apparatus which, used daily, is likely to be carried when travelling.

Another possible variation consists in constructing the apparatus in two blocks separated along the dotted line A—A of FIG. 2. The transformer—rectifier unit may moreover in this case, be formed by a commercial device, of the type used for supplying pocket calculators.

It is of course to be understood finally that the invention is not limited to an apparatus providing two heating periods and three heating temperatures. All the combinations of periods and temperatures may be contemplated.

We claim:

1. An apparatus for the heat treatment of contact lenses, selectively permitting either the heating of the lenses while subjected to an anti deposit treatment for the removal of deposits which settle thereon, at 30 to 40 degrees Celsius for about one hour or the heating of the lenses at 56–58 degrees Celsius for at least 3 hours for asepticizing lenses contaminated by the normal bacterial flora of the eye of the type comprising a box having a housing adapted to receive a case for contact lenses and including an electrical circuit comprising a power supply and at least two heating units each comprising one heating resistor and a heat-sensitive switch device for controlling the heat gener-ated by said heating resistor within, respectively, the 30° to 40° C. and 56° to 58° C. temperatures characterized in that it comprises an electronic voltage threshold detection for interrupting current flow to said respective heating resistor and a programmed control device for controlling said threshold detection to supply current to said respective heating resistor for about one hour at said 30 to 40 degrees Celsius and for at least 3 hours at said 56 to 58 degrees Celsius, said programmed control device including switch means which selectively supplies current to the selected heating unit.

2. An apparatus according to claim 1, characterized in that it is supplied with DC or rectified current and in that the voltage threshold detection and programmed control device is formed by a unit comprising an integrator connected:

firstly, to the power supply, secondly, to a potentiometer, and thirdly, to a threshold detector inserted in the heating unit circuit, said integrator delivering an output voltage which is compared to the tripping value of the threshold detector, which value is fixed by the potentiometer, the threshold detector switching and interrupting the current flow when said output voltage is equal to said value.

3. An apparatus according to claim 2, characterized in that it is supplied with current by means of a commercial cell or a battery of cells.

4. An apparatus according to claim 1 further comprising a third heating unit for asepticization of contact lenses by heating the lenses at 85 to 100 degrees Celsius for at least 3 hours to asepticize lenses abnormally contaminated compared with contamination resulting from the normal bacterial flora of the eye characterized in that a third heating unit is controlled so as to maintain a temperature between 85° and 100° C.

5. An apparatus according to claim 1, characterized in that the heat-sensitive device with which the apparatus is provided is formed by a thermistor of the PCT type chosen according to the temperature to be maintained constant.

* * * * *